US006436401B1

United States Patent
McMichael (12)

(10) Patent No.: US 6,436,401 B1
(45) Date of Patent: Aug. 20, 2002

(54) METHODS FOR ALLEVIATING SYMPTOMS ASSOCIATED WITH DIABETES AND DIABETIC NEUROPATHY COMPRISING ADMINISTRATION OF LOW LEVELS OF ANTIBODIES

(75) Inventor: John McMichael, Delanson, NY (US)

(73) Assignee: Milkhaus Laboratory, Inc., Delanson, NY (US)

( * ) Notice: Subject to any disclaimer, the term of this patent is extended or adjusted under 35 U.S.C. 154(b) by 0 days.

(21) Appl. No.: 09/918,343

(22) Filed: Jul. 30, 2001

Related U.S. Application Data

(63) Continuation-in-part of application No. 09/774,770, filed on Jan. 31, 2001, now Pat. No. 6,294,171, which is a continuation-in-part of application No. 09/514,993, filed on Feb. 29, 2000, now Pat. No. 6,187,309.
(60) Provisional application No. 60/153,838, filed on Sep. 14, 1999.

(51) Int. Cl.⁷ ............................................. A61K 39/395
(52) U.S. Cl. ................. 424/145.1; 424/146.1
(58) Field of Search ........................... 424/145.1, 146.1

(56) References Cited

U.S. PATENT DOCUMENTS

| | | | |
|---|---|---|---|
| 4,384,993 A | 5/1983 | Sato et al. ............... 260/112 B |
| 4,692,331 A | 9/1987 | Uemura et al. ................ 424/85 |
| 5,645,998 A | 7/1997 | Atkinson et al. ............. 435/7.4 |
| 5,762,937 A | 6/1998 | Atkinson et al. ......... 424/198.1 |
| 5,792,620 A | 8/1998 | Lernmark et al. .......... 435/7.95 |
| 6,001,360 A | 12/1999 | Atkinson et al. ......... 424/185.1 |
| 6,011,139 A | 1/2000 | Tobin et al. ............ 530/388.26 |
| 6,025,176 A | 2/2000 | Lernmark et al. ........... 435/195 |
| 6,187,309 B1 * | 2/2001 | McMichael et al. ...... 424/159.1 |
| 6,294,171 B2 * | 9/2001 | McMichael .............. 424/150.1 |
| 6,300,089 B1 | 10/2001 | Atkinson et al. ........... 435/7.24 |

FOREIGN PATENT DOCUMENTS

| | | | |
|---|---|---|---|
| CA | 2232834 | 3/1997 | .......... A61K/39/44 |
| WO | WO 92/20811 | 11/1992 | .......... C12P/19/34 |
| WO | WO 97/10847 | 3/1997 | .......... A61K/39/44 |

OTHER PUBLICATIONS

Blanas et al., "Induction of Autoimmune Diabetes by Oral Administration of Autoantigen," *Science*, 274:1707–1709 (1996).

Graves et al., "Lack of Association Between Early Childhood Immunizations and β–Cell Autoimmunity," *Diabetes Care*, 22:1694–1697 (1999).

Kaufman et al., "Spontaneous Loss of T–Cell Tolerance to Glutamic Acid Decarboxylase in Murine Insulin–Dependent Diabetes," *Nature*, 366:69–72(1993).

Tian et al., "Modulating Autoimmune Responses to GAD Inhibits Disease Progression and Prolongs Islet Graft Survival in Diabetes–Prone Mice," *Nat. Med.*, 2:1348–1353 (1996).

Tisch et al., "Immune Response to Glutamic Acid Decarboxylase Correlates with Insulitis in Non–Obese Diabetic Mice," *Nature*, 366:72–75 (1993).

Ramiya et al., "Effect of Oral and Intravenous Insulin and Glutamic Acid Decarboxylase in NOD Mice," *Autoimmunity*, 26:139–151 (1997).

Song et al., "Human Insulin B Chain but not A Chain Decreases the Rate of Diabetes in BB Rats," *Diabetes Research and Clinical Practice*, 46:109–114 (1999).

\* cited by examiner

*Primary Examiner*—Raymond Henley, III
(74) *Attorney, Agent, or Firm*—Marshall, Gerstein & Borun

(57) ABSTRACT

The invention provides methods and compositions for alleviating the symptoms of diabetes with a pharmaceutical composition including a combination of anti-glutamic acid decarboxylase (anti-GAD) and anti-insulin antibodies.

16 Claims, No Drawings

METHODS FOR ALLEVIATING SYMPTOMS ASSOCIATED WITH DIABETES AND DIABETIC NEUROPATHY COMPRISING ADMINISTRATION OF LOW LEVELS OF ANTIBODIES

This application is a continuation-in-part of U.S. application Ser. No. 09/774,770 filed on Jan. 31, 2001 and issued as U.S. Pat. No. 6,294,171 which is a continuation-in-part of U.S. application Ser. No. 09/514,993 filed on Feb. 29, 2000 and issued Feb. 13, 2001 as U.S. Pat. No. 6,187,309, which claims benefit of U.S. Provisional Application Ser. No. 60/153,838 filed on Sep. 14, 1999; the disclosures of which are hereby incorporated by reference.

BACKGROUND OF THE INVENTION

The therapeutic use of antibodies is generally limited to: (a) immunotherapy, where a specific antibody directed against a discreet antigen is used to counter the effect of that antigen, e.g., using an antitoxin administered to neutralize a toxin, or antibody against an infectious agent to interrupt the pathophysiological process induced by that target organism; (b) the administration, often i.v., of high levels of antibody (gamma globulin therapy) to compensate for transient or permanent immune deficiency; and (c) monoclonal antibody therapy to combat cancer, certain autoimmune disorders and metabolic diseases. In all these cases, antibody is provided in relatively high concentrations for the purpose of having that antibody combine directly with its target antigen to render that antigen inoperable, non-infectious or neutralized. For example, Gamimune™ (Bayer Biological) contains 50 mg protein (immunoglobin) per mL and normal dosing can be up to 1000 mg/kg body weight. Gammar—P™ I.V. (Aventis Behring) is administered at dosages up to 400 mg/kg body weight. Bayhep B™ (Hepatitis B Immunoglobulin) (Bayer Biological) is 15–18% protein [immunoglobulin] is administered at dosages of up to 0.6 ml/kg body weight=0.01 g/kg=100 mg/kg. Further, Imogam Rabies—HT™ (Aventis Pasteur) is 10–18% protein and is administered at a dosage of 0.133 ml/kg (240 mg/kg) body weight.

Diabetes mellitus is a metabolic disease state that is caused by a deficiency of insulin (Type I diabetes) or by the body's resistance to diabetes (Type II diabetes). The disease is characterized by chronic hyperglycemia, glycosuria, water and electrolyte loss, ketoacidosis, neuropathy, retinopathy, nephropathy, increased susceptibility to infection, and coma. Type I diabetes results from the autoimmune destruction of beta cells of the pancreas. Thus, proteins produced by beta cells have been a prime target in the study of diabetes as potential autoantigens that serve as the target for the immune response against the beta cells. One autoantigen found to correspond to the onset of Type I diabetes is glutamic acid decarboxylase (GAD) [Tisch, Roland, et al., Nature, 366:72–75 (1993)]. Another example of a beta cell autoantigen is insulin.

Much of the research involving the autoimmune response against beta cells or the autoantigens thought to be involved in the autoimmune response has included the administration of autoantigens, immunogenic portions of autoantigens, or molecules that mimic the autoantigens. Tian, Jide, et al., Nat Med, 2(12): 1348–53(1996) discusses administration of GAD to alter the diverse immune response that can lead to diabetes. Ramiya, Vijayakumar K., et al., Autoimmunity, 26:139–151(1997) discussed administration of insulin and GAD in nonobese diabetic mouse to achieve anti-diabetic affects.

Of interest to the present application is the disclosure of co-owned U.S. Pat. No. 6,187,309, which is directed to the administration of anti-rubeola antibodies for the treatment of symptoms of various central nervous system diseases including autism, multiple sclerosis, attention deficit disorder (ADD) and attention deficit hyperactivity disorder (ADHD). Examples therein demonstrated the efficacy of treating the symptoms of those disease states with dosages of from 0.1 mg to 1 mg of anti-rubeola antibody per dose.

While the administration of larger quantities of immunoglobulins is effective in the treatment of many disease states, there remains a desire in the art for methods for the treatment and prevention of diabetes.

SUMMARY OF THE INVENTION

The present invention is directed to the discovery that the symptoms diabetes may be effectively treated by administration of very low levels of a combination of anti-glutamic acid decarboxylase (anti-GAD) antibodies and anti-insulin antibodies. Specifically, the antibodies may be administered in one or in multiple dosages but the sum of antibodies administered in any 24 hour period (or daily period) is less than 10 mg each of anti-GAD and anti-insulin antibodies, with preferred daily dosages being less than 1.0 mg and more preferably less than 0.1 mg.

While the antibody may be monoclonal or polyclonal, it is preferably monoclonal according to one aspect of the invention. The antibody may be administered by a variety of manners but is preferably administered subcutaneously and orally. Suitable methods of oral administration include oral drench and sublingual administration. According to another aspect of the invention the antibody is administered in an enterically protected form.

The invention provides methods for treating the symptoms of diabetes comprising the method of administering an effective amount of a combination of an antibody directed against GAD and antibody directed against insulin. The term "effective amounts of an antibody" is used herein to describe the amount of antibody administered to a subject to result in the reduction or elimination of the pathogenic autoimmune response associated with the onset of diabetes, thereby alleviating symptoms of diabetes. Preferred amounts of anti-GAD and anti-insulin antibodies for use according to the disclosed method are less than 1.0 mg of anti-GAD antibodies and less than 1.0 mg of anti-insulin antibodies, and more preferably less than 0.1 mg of anti-GAD antibodies and less than 0.1 mg of anti-insulin antibodies. A still more preferred daily dosage ranges from $1\times10^{-6}$ to $1\times10^{-2}$ mg of anti-GAD antibodies and $1\times10^{-6}$ to $1\times10^{-3}$ insulin antibodies. An even more preferred daily dosage ranges from $1\times10^{-5}$ to $1\times10^{-3}$ mg of anti-GAD antibodies and $1\times10^{-5}$ to $1\times10^{-3}$ mg of anti-insulin antibodies.

The invention also provides pharmaceutical compositions for administration to subjects for treatment of the symptoms of diabetes comprising a dosage unit of less than 10 mg of anti-GAD antibodies and less than 10 mg of anti-insulin antibodies. A preferred dosage unit is less than 1.0 mg of anti-GAD antibodies and less than 1.0 mg of anti-insulin antibodies, and more preferably less than 0.1 mg of anti-GAD antibodies and less than 0.1 mg of anti-insulin antibodies. A still more preferred dosage unit ranges from $1\times10^{-6}$ to $1\times10^{-2}$ mg of anti-GAD antibodies and $1\times10^{-6}$ to $1\times10^{-2}$ mg of anti-insulin antibodies. An even more preferred dosage unit ranges from $1\times10^{-5}$ to $1\times10^{3}$ mg of anti-GAD antibodies and $1\times10^{-5}$ to $1\times10^{-3}$ mg of anti-insulin antibodies.

DETAILED DESCRIPTION

The methods and compositions described herein relate to low levels of antibodies specific for the autoantigens of pancreatic beta cells that can reduce or eliminate the pathological consequences caused by the autoimmune response against the pancreatic beta cells. The mechanism by which this is accomplished is not completely understood and is the focus of ongoing research. Without intending to be bound by any particular theory of the invention, it is thought that the low levels of the antibodies specific for the autoantigens are able to prevent the pathogenic cascade that results from the destruction of the autoantigens by the immune system, possibly by redirecting the host immune system or by providing a negative feedback to prevent further autoimmune response. Particularly, the use of antibodies against GAD and insulin can be used as a systemic signal to specifically inhibit the body's aberrant, pathogenic response to the autoimmune response against GAD and insulin. In addition to the use of the disclosed method to alleviate symptoms of diabetes, it is further contemplated that practice of the methods disclosed herein will prove useful in the prevention of diabetes.

Antibodies of the invention can be produced using any method well known and routinely practiced in the art. Such antibodies include monoclonal and polyclonal antibodies, single chain antibodies, chimeric antibodies, bifunctional/bispecific antibodies, humanized antibodies, human antibodies, and complementary determining region (CDR)-grafted antibodies, including compounds which include CDR and/or antigen-binding sequences, which specifically recognize a polypeptide of the invention. A preferred anti-GAD antibody and anti-insulin antibody is available from Chemicon International Inc., Temecula, Calif.

Symptoms of diabetes which can be treated according to the methods of the invention include elevated blood sugar level, elevated hemoglobin A1c level, neuropathy, retinopathy, ketoacidosis, and glycosuria. With respect to blood sugar levels, normal levels are <140 mg/dl, and diabetic levels are considered to be levels >140 mg/dl.

The following examples are illustrative and are not intended to limit either the scope or spirit of the invention.

EXAMPLES

Example I

According to this example, low dosages of a combination of anti-GAD and anti-insulin antibodies were administered to a 3–4 year old female cat with a blood glucose level of 352 mg/dl. The cat experienced the traditional symptoms of diabetes, which included weight loss and dehydration among others. Specifically, the subject was treated by subcutaneous injection twice daily of one dose of anti-GAD ($8\times10^{-4}$ mg) and anti-insulin antibodies ($4\times10^{-4}$ mg). Antibodies used were sheep polyclonal antibodies and both the anti-GAD and anti-insulin antibodies were obtained from Chemicon International Inc., Temecula, Calif. In about 5 days the subject had a reduced blood glucose level of 110 mg/dl. This treatment was stopped at day 10 with the subject having a blood glucose level of 82 mg/dl. Subsequent testing of the subject showed that after about 3 weeks after treatment was stopped, the subject was alleviated of diabetic symptoms without subjection to additional therapy.

Example II

According to this example, a spayed 10 year old Rottweiler with insulindependent diabetes had required 42 units of insulin twice daily. The subject had a blood glucose level of 371 mg/dl even with the administration of insulin on day 1 of therapy with anti-GAD and anti-insulin antibodies. The subject was treated by subcutaneous injection twice daily of one dose of anti-GAD ($8\times10^{-4}$ mg) and anti-insulin antibodies ($4\times10^{-4}$ mg). The antibodies used in this example are the same as that used above in Example I. After about 5 weeks of treatment with decreasing insulin dosage, the subject had a reduced blood glucose level of 165 mg/dl.

Example III

According to this example, a 13 year old neutered male domestic long hair cat experiencing anorexia, depression and having collapsed was subjected to antibody therapy. The subject had a blood glucose level of 473 mg/dl initially. The subject was treated by subcutaneous injection twice daily of one dose of anti-GAD ($4\times10^{-4}$ mg) and anti-insulin antibodies ($2\times10^{-4}$ mg) in addition to insulin dosage of 1.3 units twice daily. The antibodies used in this example are the same as that used above in Example I. On day 13 the subject had a reduced blood glucose level of 41 mg/dl in the morning and 44 mg/dl in the afternoon, and the insulin dosage was reduced to 0.8 units twice daily. On day 18 the subject had a blood glucose level of 81 mg/dl and the insulin dosage was eliminated. After approximately 3 months of antibody treatment and no insulin for about 1 month, the subject had a blood glucose level of 99 mg/dl.

Example IV

According to this example, a 8 year old neutered female domestic shorthair cat had a blood glucose level of 369 mg/dl and had undergone treatment with insulin, 3.0 units bid. With a blood glucose level of 439 mg/dl, the subject underwent antibody therapy comprising subcutaneous injection twice daily of one dose of anti-GAD ($8\times10^{-4}$ mg) and anti-insulin antibodies ($4\times10^{-4}$ mg). The antibodies used in this example are the same as that used above in Example I. After about 3.5 weeks of therapy, insulin treatment was reduced to 2.5 units bid. After 5 weeks the blood glucose level was reduced to 125 mg/dl. After about 4 months, the subject had a blood glucose level of 105 mg/dl. The subject eventually was removed from insulin therapy and kept on low level antibody therapy.

Example V

According to this example, a 45 year old female diagnosed with insulindependent diabetes was treated with low level antibodies. The subject was determined to have a hemoglobin AlC level of 11%, which is typically at a level of 4–6% in non-diabetic individuals. The subject experienced neuropathy characterized by numbness and poor circulation as determined by the subject in response to a tuning fork test. The subject underwent antibody therapy by sublingual administration, via drops, twice daily of one dose of anti-GAD ($8\times10^{-4}$ mg) and anti-insulin antibodies ($4\times10^{-4}$ mg). The antibodies used in this example are the same as that used above in Example I. The subject was tested for hemoglobin AlC levels after 2 weeks of therapy and the levels were reduced to 7%. The subject was free from any other therapies during the low level antibody therapy. After one week the subject experienced a disappearance of neuropathy in the subject's lower extremities. The low level antibody treatment was stopped and the subject's previously experienced neuropathy returned after approximately one week.

Example VI

According to this example, a 42 year old female with a 20 year history of diabetes mellitus was treated with low level antibodies. The subject was treated with antibody therapy by sublingual administration in the form of 1 drop (or dose), 4× per day. Each dose contained $8 \times 10^{-4}$ mg of anti-GAD and $4 \times 10^{-4}$ mg of anti-insulin antibodies. The antibodies used in this example are the same as that used above in Example I. After approximately one week, the subject experienced an abatement of pain from diabetic neuropathy and a reduction in blood sugar levels. Following a one week period in which the subject experience no pain, the subject was discontinued from low level antibody treatment. The discontinuation resulted in reoccurrence of diabetic neuropathy and elevated blood sugar levels, which were the symptoms experience by the subject prior to low level antibody treatment. Subsequently, the subject was, again, treated with low level antibody therapy, which resulted in abatement of pain from diabetic neuropathy and a reduction in blood sugar levels similar to the result from the initial therapy with low level antibodies.

Example VII

According to this example, a white male diagnosed with diabetes was treated with low level antibodies. The subject was treated with antibody therapy by sublingual administration in the form of I drop (or dose), 2× per day. Each dose contained $8 \times 10^{-4}$ mg of anti-GAD and $4 \times 10^{-4}$ mg of anti-insulin antibodies. The antibodies used in this example are the same as that used above in Example I. After approximately eight weeks the subject experienced a reduction in diabetic neuropathy of approximately 60%. This reduction in diabetic neuropathy was determined by having the patient assess the sensations resulting from a tuning fork on the subject's lower extremities just prior to treatment and after the eight weeks of treatment. Additionally, the subject experienced a loss in weight (approximately 12 lbs.), increased energy and a reduction in levels of blood sugar of about 40 mg/dl.

Numerous modifications and variations in the practice of the invention are expected to occur to those skilled in the art upon consideration of the presently preferred embodiments thereof. consequently, the only limitations which should be placed upon the scope of the invention are those which appear in the appended claims.

What is claim is:

1. A method of alleviating symptoms of diabetes, comprising the step of administering the combination of anti-glutamic acid decarboxylase (anti-GAD) antibody and anti-insulin antibody in amounts effective to alleviate symptoms of diabetes.

2. The method of claim 1, wherein the symptoms are selected from the group consisting of elevated blood sugar level, elevated hemoglobin A1c level, neuropathy, retinopathy, ketoacidosis, and glycosuria.

3. The method of claim 1 wherein both anti-GAD and anti-insulin antibodies are monoclonal antibodies.

4. The method of claim 1 wherein the administration step is oral.

5. The method of claim 4 wherein the administration step is sublingual.

6. The method of claim 4 wherein both anti-GAD and anti-insulin antibodies are administered in an enterically protected form.

7. The method of claim 1 wherein the administration step is by injection.

8. The method of claim 7 wherein the administration step is by subcutaneous injection.

9. The method of claim 1 comprising less than 1.0 mg of anti-GAD antibodies and less than 1.0 mg of anti-insulin antibodies.

10. The method of claim 9 comprising less than 0.1 mg of anti-GAD antibodies and less than 0.1 mg of anti-insulin antibodies.

11. The method of claim 9 comprising from $1 \times 10^{-6}$ to $1 \times 10^{-2}$ mg of anti-GAD antibodies and $1 \times 10^{-6}$ to $1 \times 10^{-2}$ mg of anti-insulin antibodies.

12. The method of claim 9 comprising from $1 \times 10^{-5}$ to $1 \times 10^{-3}$ mg of anti-GAD antibodies and $1 \times 10^{-5}$ to $1 \times 10^{-3}$ mg of anti-insulin antibodies.

13. A pharmaceutical composition for administration to a subject for alleviating symptoms of diabetes comprising less than 1.0 mg of anti-GAD antibodies and less than 1.0 mg of anti-insulin antibodies.

14. A pharmaceutical composition of claim 13 comprising less than 0.1 mg of anti-GAD antibodies and less than 0.1 mg of anti-insulin antibodies.

15. A pharmaceutical composition of claim 13 comprising from $1 \times 10^{-6}$ to $1 \times 10^{-2}$ mg of anti-GAD antibodies and $1 \times 10^{-6}$ to $1 \times 10^{-2}$ mg of anti-insulin antibodies.

16. A pharmaceutical composition of claim 13 comprising from $1 \times 10^{-5}$ to $1 \times 10^{-3}$ mg of anti-GAD antibodies and $1 \times 10^{-5}$ to $1 \times 10^{-3}$ mg of anti-insulin antibodies.

* * * * *